United States Patent [19]
Turner

[11] Patent Number: 5,211,286
[45] Date of Patent: * May 18, 1993

[54] PERSONAL IDENTIFICATION SYSTEM

[76] Inventor: Mike L. Turner, 811 Bradford St., N.W., Gainesville, Ga. 30501

[*] Notice: The portion of the term of this patent subsequent to Apr. 7, 2009 has been disclaimed.

[21] Appl. No.: 863,853

[22] Filed: Apr. 6, 1992

Related U.S. Application Data

[63] Continuation of Ser. No. 580,094, Sep. 10, 1990, Pat. No. 5,101,970.

[51] Int. Cl.$^5$ .................. A01N 1/00; B65D 43/16
[52] U.S. Cl. .................. 206/223; 53/440; 53/449; 206/803
[58] Field of Search .......... 118/31.5; 53/440, 449; 206/223, 232, 438, 459, 570-572, 803

[56] References Cited

U.S. PATENT DOCUMENTS

| | | | |
|---|---|---|---|
| 2,655,152 | 10/1953 | Turner et al. | 206/223 |
| 3,061,087 | 10/1962 | Scrivens et al. | 118/31.5 |
| 3,255,871 | 6/1966 | Butler | 206/438 |
| 3,709,524 | 1/1973 | McKee et al. | 118/31.5 |
| 3,911,918 | 10/1975 | Turner | 206/438 |
| 4,122,947 | 10/1978 | Falla | 206/569 |
| 4,472,357 | 9/1984 | Levy et al. | 206/459 |
| 4,669,753 | 6/1987 | Land et al. | 118/31.5 |
| 4,777,964 | 10/1988 | Briggs et al. | 206/569 |
| 4,844,259 | 7/1989 | Glowczewskie, Jr. et al. | 206/370 |

FOREIGN PATENT DOCUMENTS 0054221  6/1982  European Pat. Off. ........... 206/438

OTHER PUBLICATIONS

Custom Forensic Kits for Hospital and Crime Laboratory Use, Tri-Tech, Inc., Forensic Kit Division, 12 page brochure.

Primary Examiner—Jimmy G. Foster
Attorney, Agent, or Firm—Hopkins & Thomas

[57] ABSTRACT

The present invention is a system for in-home collection and preservation of information for identifying and locating lost or missing loved ones. The system includes devices for collecting, sealing, and preserving hair, blood, and fingerprint samples from each loved one and for recording vital person data regarding each loved one. The information and samples are collected, sealed and stored in the family freezer to insure that the collected specimens remain viable indica of identification for long subsequent periods of time.

10 Claims, 1 Drawing Sheet

PERSONAL IDENTIFICATION SYSTEM

This application is a continuation of U.S. application Ser. No. 580,094, filed Sep. 10, 1990, now U.S. Pat. No. 5,101,970.

TECHNICAL FIELD

This invention relates to personal identification and particularly to a system for in-home collection and preservation of information for identification in the event of a missing or lost loved one.

BACKGROUND OF THE INVENTION

It has long been common to collect and preserve identifying information on virtually everything of value for insurance purposes in the event of theft or natural disaster. Curiously, however, identifying information about our most valuable assets, namely our loved ones, is seldom collected and preserved for use in the event a family member is abducted or otherwise becomes missing. This is indeed unfortunate since such information, if available, can be the critical link to evidence that could help identify, locate and possibly save the life of a missing loved one. Hair sample comparison and DNA print matching, for example, might be used by forensic pathologists to identify an unknown hair, blood, or tissue sample as that of a missing person, thereby generating a lead to locating such person. Furthermore, the simple recording of data such as a recent photograph, hair color, eye color, identifying marks, etc. can be invaluable in locating a missing child, for example, since such information can be quickly and widely disseminated among the public.

Tragically, some missing persons are victimized and killed by their abductors who often leave their victim's body in an isolated or inaccessible location. When such bodies are eventually found, they are often so deteriorated that identification through traditional means is impossible. In these instances, techniques such as DNA print matching can still provide a positive identification since every cell in an individual's body, even the cells of deteriorated remains, contains DNA cells having gene patterns that are unique to that individual alone. Sadly, however, DNA analysis is seldom fruitful in this regard because cell bearing specimens from only a minute fraction of missing persons are available for comparison to those of unidentified remains. As a consequence, many remains are never identified and, in fact, government agencies estimate that as many as 2000 unidentified bodies are buried each year in the U.S. alone. In the mean time, the families of these unidentified people will continue to grieve, not knowing whether their loved one is alive or dead.

A continuing and heretofore unaddressed need exists, therefore, for a system of collecting and preserving vital identifying information about and cell bearing specimens from family members and loved ones for use in the event a loved one becomes missing. Such a system should be complete, convenient, easy to use in the home without medical supervision and should be adapted to preserve cell bearing specimens such as blood for long periods without significant deterioration of the specimens. It is to the provision of such a system that the present invention is primarily directed.

SUMMARY OF THE INVENTION

The present invention comprises an in-home system for collecting and preserving a complete identification record of loved ones for use in the unfortunate event a loved one becomes missing. The system embodies the process of collecting and recording various information regarding loved ones, including fingerprints, vital information, hair samples, and blood samples; sealing the collected samples and information against deterioration and freezing at least the cell bearing specimens to insure the longevity and integrity thereof.

The system further comprises an identification kit for implementing the method of the invention. The kit includes devices for collecting and recording vital data and DNA bearing specimens and sealing the information and specimens in a container for storage in a home freezer. In use, vital data, fingerprints, blood samples, and hair samples are collected from each loved one, sealed, and placed in a home freezer for preservation. Should a loved one become missing, the preserved data for that person can be delivered to law enforcement agencies for use in locating and identifying the missing loved one.

It is thus an object of this invention to provide a convenient, easy to use, and inexpensive system for collecting and preserving a complete identification record of loved ones.

Another object of the invention is to provide a system for assisting law enforcement agencies in locating and identifying missing persons.

A further object of the invention is to provide loved ones with the peace of mind in knowing that should one of them become missing, a complete record for use in location and identification is readily available.

These and other objects, features, and advantages of the invention will become more apparent upon review of the following detailed description when taken in conjunction with the accompanying drawings.

DETAILED DESCRIPTION OF THE PREFERRED EMBODIMENT

Figure 1:
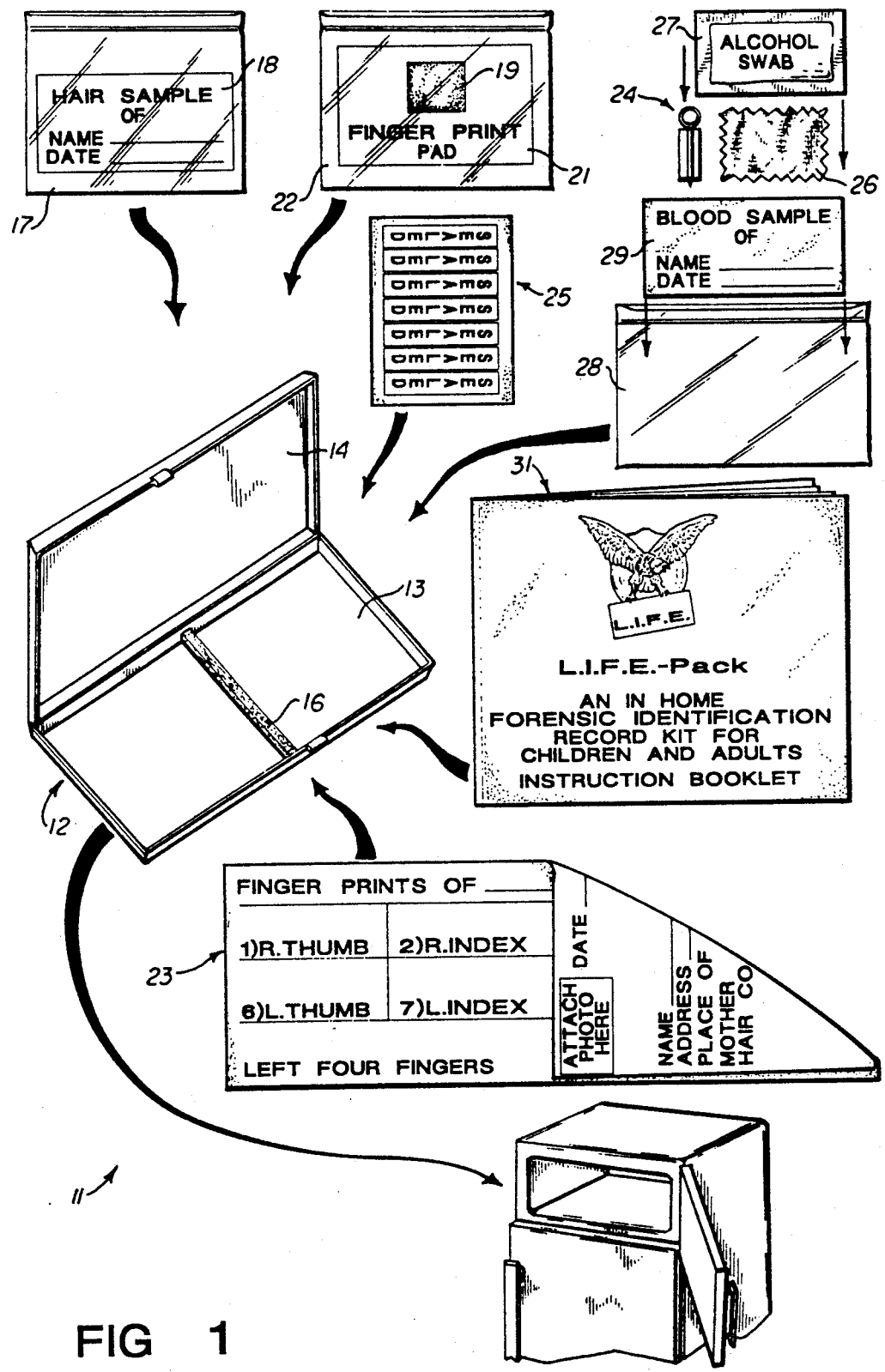
FIG. 1 is a perspective partially exploded view of a personal identification system that embodies principles of the invention in a preferred form.

Referring now in more detail to the drawing, in which reference numerals refer to salient elements of the preferred embodiment, FIG. 1 illustrates an identification system 11 that embodies principles of the invention in a preferred form. The system 11 includes a case 12 that is preferably formed of clear plastic and that includes a base member 13 having a hinged lid 14. A partition 16 is positioned within the base member 13 and subdivides it into two distinct storage areas.

The system is provided with a number of devices for collecting and preserving data and physical evidence from an individual for identification. More specifically, means for collecting and storing a sample of an individual's hair includes a sealable plastic envelope 17 adapted to receive the hair sample and to receive a card 18 bearing the date of the sample and the identity of the person from whom the sample was taken.

Means for capturing and preserving the fingerprints of the individual includes a fingerprint pad 19 that is impregnated with fingerprint ink and secured to a support card 21. The pad and card are in turn enclosed within a sealable plastic envelope 22 to prevent the pad from drying out prior to use. An identification card 23 has printed on one side a matrix for receiving the fingerprints of an individual in the usual way. The array includes positions for fingerprints of each finger of each hand as well as positions for prints of several fingers taken in conjunction. Space for providing the identity of the person whose fingerprints appear on the card is also provided.

Means for collecting and securing a sample of an individual's blood for use in DNA print identification includes a lancing tool 24 for piercing the tip of a finger to draw blood, a cloth patch 26 for receiving and securing a sample of the blood, and a sterile swab 27 for wiping the pricked finger before and after the blood sample has been taken. A sealable plastic envelope 28 is sized to receive and seal the patch 26 and blood sample thereon and a card 29 is provided for identifying the date of the sample and the person whose blood is contained within the patch 26.

Printed on the side of card 23 opposite the fingerprint matrix is a form for recording vital personal data regarding the individual whose identity is being secured. This form includes positions for recording the image of the individual through a photograph as well as other vital data such as name, address, place of birth, date of birth, hair color, eye color, etc. Such data can be and often is valuable in identifying persons who are alive but who may have lost their memories, grown older or disguised their identity.

Also included with the system is a booklet 31 that contains vital information regarding modern methods used in identifying individuals and that includes detailed instructions for use of the system of the present invention to secure the identities of loved ones. A set of decals 25 each imprinted with the word "SEALED" are provided for securing the collected data and specimens as detailed below.

USE OF THE SYSTEM

Use of the system of this invention to collect and preserve vital data about and physical specimens from loved ones is simple and easily carried out in the home. First, a photograph of each loved one is secured and attached to the corresponding identification card 23. All of the information solicited on the card is then entered in the spaces provided on the card.

The card 23 can then be turned over such that its fingerprint matrix faces up for recording fingerprints. In this regard, the fingerprint pad 19 and its support card 21 are removed from their sealed envelope 22. Each finger of the person being identified is then rolled slowly across the inked pad to deposit the fingerprint ink onto the fingertips. The fingers are then rolled in sequence across the card 23 in the positions of the matrix corresponding to each finger. Prints of the four fingers of the left and right hands are taken simultaneously and applied to their proper positions within the fingerprint matrix. The identification and fingerprint card 23 is thus completed and the fingerprint pad and its sealed envelope can be discarded if desired.

Next, a sample of the individual's hair is taken and prepared for preservation. Preferably, several hairs are cut from the individual's head and secured to the back of the card 18 with a staple or tape. The sample is then set aside to air dry for approximately one hour such that oil and other fluids can evaporate from the sample. This drying time is important because fluids contained within freshly cut hair samples can accelerate the deterioration of the samples if they are sealed along with the samples. Once the hair sample has dried for the specified time, the identification of the individual from whom the sample was taken and the date it was taken are provided on the card and the card and its attached sample are secured and sealed within the plastic envelope 17.

Finally, a sample of the individual's blood is collected and prepared for preservation. In this regard, the cloth patch 26, lancing tool 24, and sterile swab 27 are obtained and the end of the lancing tool is twisted off to reveal its blade. A fingertip of the individual being identified is then wiped with the swab and pierced quickly with the lancing tool to draw a small amount of blood from the finger. The patch 26 is applied to the fingertip to absorb the blood for preservation. The blood impregnated patch is then set aside for approximately one hour to allow unwanted fluids to evaporate from the blood sample. As with the hair sample, these fluids can accelerate the deterioration of the blood if sealed therewith such that the drying process is important for maximum longevity of the sample. The identification of the individual whose blood sample has been taken and the date the sample was taken are then provided on the card 29 and the card and blood impregnated patch 26 are secured and sealed within the plastic envelope 28.

With the hair and blood sample thus taken, dried and sealed within their envelopes, one of the adhesive decals 25 can be secured over the top edge of each envelope to insure that the contents of the envelopes are not subsequently tampered with or altered. The sealed and secured bags containing the hair and blood samples and the card 23 containing the fingerprints and vital data are then placed within the case 12 for storage. Preferably, data and samples for a number of loved ones, four for example, can be taken in the above described manner and placed within a single case 12. With the data and samples thus placed, the case 12 is closed by hinging its lid 14 shut over its base 13. A final one of the adhesive decals 25 can then be secured across a closed edge of the case to insure against tampering.

With the vital identifying information of all loved ones secured and sealed within their respective envelopes and within the case, the entire case can be placed within the family freezer for storage. In the freezer, the blood and hair samples are chilled to a temperature below their freezing point such that the useful life of these samples is extended long beyond that which they would exhibit under normal temperature conditions. Further, the low temperature within the freezer tends to enhance the longevity of the fingerprints and slows the aging and deterioration of photographs and other identifying information. Typically, specimens stored within the freezer can be expected to last and be usable for identification for a number of years whereas specimens stored at normal room temperatures may only last for a few weeks. It is therefore important that the specimens be stored within the freezer to insure their viability should they ever be needed to identify a missing loved one.

The invention has been described above in terms of a preferred embodiment. It will be obvious, however, that many variations of the illustrated embodiment might well be contemplated by ordinarily skilled artisans. The order in which information and samples are taken and sealed can, for example, be different than that illustrated above. Further, various means for sealing the hair and blood samples could also be used with results comparable to that of the sealable plastic envelopes of the preferred embodiment. Also, other types of sample such as, for example, skin tissue samples, could also be used with the illustrated system to provide specimens for DNA print analysis. These and other modifications, deletions and additions might well be made to the illustrated embodiment without departing from the spirit and scope of the invention as set forth in the claims.

I claim:

1. A method of collecting and preserving body identification information of a person for later use in identifying the person, comprising:

recording identifying data about the person on card means, collecting in proximity with the card means at least one specimen from the person, the specimen including identifying cells of the person, placing the card means and specimen in a storage container sealed from the atmosphere, and maintaining the card, specimen and storage container at a temperature low enough to retard temporal deterioration of the specimen.

2. The method of collecting and preserving body identification information of a person as set forth in claim 1 and wherein the step of collecting in the proximity of the card means at least one specimen from the person comprises drawing blood from the person and blotting the blood from the person on an absorbent patch which is maintained with the card means in the storage container.

3. The method of collecting and preserving body identification information of a person as set forth in claim 2 and wherein the step of placing the card means and specimen in storage containers sealed from the atmosphere comprises placing the card means and specimen in a flexible plastic bag and sealing the bag.

4. The method of collecting and preserving body identification information of a person as set forth in claim 1 and wherein the step of collecting in proximity with the card means at least one specimen from the person comprises collecting a liquid specimen from the person and drying the specimen, and wherein the step of placing the card means and specimen in a storage container sealed from the atmosphere comprises sealing the card means and specimen in the storage container after the specimen has dried.

5. The method of collecting and preserving body identification information of a person as set forth in claim 4 and wherein the step of collecting at least one specimen from the person comprises cutting hair from the person.

6. The method of collecting and preserving body identification information of a person as set forth in claim 1 and wherein the step of placing the card means and specimen in a storage container comprises placing the card member and specimen in a clear plastic container.

7. A method of collecting and preserving body identification information of a person for later use in identification of the person with said method comprising the steps of:

recording identifying data about the person on a card means with said data including at least fingerprints of the person, collecting a specimen of the individual's blood and drying the collected blood specimen, sealing the card means with its recorded identifying data together with the collected and dried blood specimen in a common storage container, and depositing the storage container bearing the data and specimen in a storage space at a temperature low enough for retarding temporal deterioration of the blood specimen.

8. A method of collecting and preserving body identification information for use in subsequent identification of the body with said method comprising the steps of:

(a) collecting and recording identifying data about the body on a card means, (b) collecting at least one specimen containing cells of the body, (c) drying the specimen, (d) sealing the collected specimen and card means against exposure to ambiance, (e) placing the sealed card means and specimen together for storage in a storage space, (f) maintaining the storage space below a predetermined temperature sufficient to retard temporal deterioration of the specimen.

9. The method of collecting and preserving body identification information as set forth in claim 8, wherein the step of collecting at least one specimen containing cells of the body comprises pricking the fingertip of the body to draw blood therefrom and depositing the blood on an absorbent patch for preservation.

10. A kit for assimilating body identification information for use in subsequent identification of the body, with said kit comprising:

card means for capturing fingerprints of the body and for receiving written identifying data of the body, a patch means supported on said card means for receiving a liquid sample taken from the body, and plastic envelope means enveloping the card means and patch means and said envelope means being sized and shaped to enclose said card means and said patch means and constructed and arranged to seal the card means and patch means against the atmosphere, so that the fingerprints of a body can be applied to and captured by the card means and blood can be taken from the body and blotted on the patch means and dried on the patch means, and the card means and patch means can be sealed in the plastic envelope means and stored in an area of temperature low enough to retard temporal deterioration of the blood.

* * * * *